(12) United States Patent
Min et al.

(10) Patent No.: US 7,139,609 B1
(45) Date of Patent: Nov. 21, 2006

(54) SYSTEM AND METHOD FOR MONITORING CARDIAC FUNCTION VIA CARDIAC SOUNDS USING AN IMPLANTABLE CARDIAC STIMULATION DEVICE

(75) Inventors: Xiaoyi Min, Thousand Oaks, CA (US); Paul A. Levine, Santa Clarita, CA (US); Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 512 days.

(21) Appl. No.: 10/346,809

(22) Filed: Jan. 17, 2003

(51) Int. Cl.
*A61B 5/02* (2006.01)
*A61N 1/365* (2006.01)

(52) U.S. Cl. ............................ 607/17; 607/24; 600/528

(58) Field of Classification Search ................ 600/508, 600/509, 513, 528, 586; 607/9, 17, 24
See application file for complete search history.

(56) References Cited

U.S. PATENT DOCUMENTS

| | | | |
|---|---|---|---|
| 5,088,491 A * | 2/1992 | Schaldach ................ 607/18 |
| 5,454,838 A | 10/1995 | Vallana et al. ............. 607/19 |
| 5,554,177 A | 9/1996 | Kieval et al. .............. 607/17 |
| 5,609,612 A * | 3/1997 | Plicchi et al. .............. 607/17 |
| 5,628,777 A | 5/1997 | Moberg et al. ............ 607/122 |
| 5,700,283 A | 12/1997 | Salo ........................ 607/17 |
| 5,792,195 A | 8/1998 | Carlson et al. ............ 607/17 |
| 5,836,987 A | 11/1998 | Baumann et al. .......... 607/17 |
| 5,935,081 A | 8/1999 | Kadhiresan ............... 600/513 |
| 5,991,661 A | 11/1999 | Park et al. ................. 607/19 |
| 6,002,963 A | 12/1999 | Mouchawar et al. ...... 607/18 |
| 6,024,705 A * | 2/2000 | Schlager et al. ........... 600/508 |
| 6,409,675 B1 | 6/2002 | Turcott ..................... 600/508 |
| 6,440,082 B1 | 8/2002 | Joo et al. .................. 600/528 |
| 6,643,548 B1 * | 11/2003 | Mai et al. .................. 607/17 |
| 6,792,308 B1 * | 9/2004 | Corbucci .................. 607/17 |
| 2002/0151812 A1 * | 10/2002 | Scheiner et al. ........... 600/528 |
| 2002/0151938 A1 * | 10/2002 | Corbucci .................. 607/25 |

OTHER PUBLICATIONS

Chew et al., "Overnight Heart Rate and Cardiac Function in Patients with Dual Chamber Pacemakers," PACE 1996; 19: 822-828.
Padmanabhan et al., "Accelerometer Type Cardiac Transducer for Detection of Low-Level Heart Sounds," IEEE Trans. Biomed. Eng., Jan. 1993; 40(1): 21-28.
Vitale et al., "Improved Hemodynamic Sensor and Lead," PACE European Suppl. vol. 3, pp. 214; Jul. 2002.

* cited by examiner

*Primary Examiner*—Robert E. Pezzuto
*Assistant Examiner*—Kristen Mullen

(57) ABSTRACT

Techniques are provided for performing internal measurement of heart sounds to estimate patient cardiac function in terms of stroke volume, cardiac output, or a maximum rate of change of aortic pressure with time (max dP/dt). Control parameters of the medical device are then automatically adjusted so as to optimize overall cardiac function or to provide for ventricular resynchronization therapy. In one example, heart sound signals are derived from acceleration signals received from an accelerometer. The heart sound signals are analyzed to identify S1 and S2 heart sounds as well as ejection period and isovolumic interval (ISOV). Proxies for max dP/dt, stroke volume and cardiac output are then derived from the S1 and S2 heart sounds, the ejection period and the ISOV. Alternative techniques, not requiring detection of ISOV, are employed for use if the patient has heart value regurgitation.

28 Claims, 7 Drawing Sheets

SYSTEM AND METHOD FOR MONITORING CARDIAC FUNCTION VIA CARDIAC SOUNDS USING AN IMPLANTABLE CARDIAC STIMULATION DEVICE

FIELD OF THE INVENTION

The invention relates generally to implantable cardiac stimulation devices, such as pacemakers or implantable cardioverter-defibrillators (ICDs), and in particular to techniques for monitoring overall cardiac function using heart sounds and other cardiac sounds and for automatically adjusting pacing parameters to improve cardiac function.

BACKGROUND OF THE INVENTION

Cardiac function is a measure of the overall effectiveness of the cardiac system of a patient and is typically represented in terms of, one or more of, stroke volume, cardiac output, end-diastolic volume, end-systolic volume, ejection fraction or cardiac output index. Stroke volume is the amount of blood ejected from the left ventricle during systole. Cardiac output is the volume of blood pumped by the left ventricle per minute (or stroke volume times the heart rate). End-diastolic volume is the volume of blood in the chamber at the end of the diastolic phase, when the chamber is at its fullest. End-systolic volume is the volume of blood in the chamber at the end of the systolic phase, when the chamber contains the least volume. Ejection fraction is percentage of the end-diastolic volume ejected by the ventricle per beat. Cardiac index is the volume of blood ejected per minute normalized to the body surface area of the patient. Other factors representative of cardiac function include the contractility of the left ventricle or the maximum rate of change of pressure with time (i.e. max dP/dt).

Overall cardiac function should be carefully monitored in patients with pacemakers or ICDs, particularly patients suffering from heart failure. Heart failure is one of the most widespread and devastating cardiac afflictions, currently affecting approximately 15 million people worldwide, including over 5 million in the United States. In the U.S., approximately 450,000 new patients are diagnosed with heart failure each year and the majority die within five years of diagnosis. One factor that contributes to heart failure is asynchronous activation of the ventricles such that the mechanical contraction is not coordinated effectively thus compromising cardiac function. As a result, the pumping ability of the heart is diminished and the patient experiences shortness of breath, fatigue, swelling, and other debilitating symptoms. The weakened heart is also susceptible to potentially lethal ventricular tachyarrhythmias. A decrease in cardiac function can result in a progression of heart failure. In many cases, pacing control parameters of the pacemaker or ICD can be adjusted to help improve cardiac function and reduce the degree of heart failure effectively reducing symptoms and improving the quality of life.

In view of the importance of maintaining adequate cardiac function, it would be desirable to provide improved techniques for use with pacemakers or ICDs for monitoring cardiac function and for automatically adjusting pacing parameters to optimize cardiac function and reduce the degree of heart failure. It is to this end that aspects of the invention are generally directed.

One particularly promising technique for reducing the risk of heart failure is "ventricular resynchronization therapy", which seeks to normalize asynchronous cardiac electrical activation and the resultant asynchronous contractions by delivering synchronized pacing stimulus to both ventricles using pacemakers or ICDs equipped with biventricular pacing capability. The stimulus is synchronized so as to help to improve overall cardiac function. This may have the additional beneficial effect of reducing the susceptibility to life-threatening tachyarrhythmias. With conventional resynchronization therapy, an external Doppler-echocardiography system may be used to noninvasively assess cardiac function. It can also be used to assess the effectiveness of any programming changes on overall cardiac function.

Then, biventricular pacing control parameters of the pacemaker or ICD are adjusted by a physician using an external programmer in an attempt to synchronize the ventricles and to optimize patient cardiac function. For example, the physician may adjust the interventricular delay, which specifies the time delay between pacing pulses delivered to the right and left ventricles, in an attempt to maximize stroke volume. To assess the effectiveness of any programming change, Doppler-echocardiography, impedance cardiography or some other independent measure of cardiac function is utilized.

However, this evaluation and programming requires an office visit and is therefore a timely and expensive process. It also restricts the evaluation to a resting state, commonly with the patient in a supine position. As such, the system is not necessarily optimized for activity, for the upright position, for other times of day since there may also be a circadian rhythm to cardiac function. It is known that heart rate and blood pressure have a diurnal variation. In a study by Chew and colleagues (See: "Overnight Heart Rate And Cardiac Function In Patients With Dual Chamber Pacemakers", Chew, et al., PACE 1996; 19: 822–828), cardiac function was shown to have a diurnal or circadian variation. Moreover, when relying on any external hemodynamic monitoring system, the control parameters of the pacemaker or ICD cannot be automatically adjusted to respond to on-going changes in patient cardiac function. Accordingly, it would be desirable to provide a technique to assess cardiac function using the implanted cardiac stimulation device. In this manner, cardiac function can be automatically evaluated and mono or biventricular pacing control parameters adjusted in a closed loop system so as to permit optimal ventricular resynchronization therapy when the patient is upright as well as supine, at various times of the day and during various activities. It is to this end that further aspects of the invention are directed.

In particular, it would be desirable to provide a technique for assessing cardiac function using heart sounds detected internally by a pacemaker or ICD. Briefly, a first (S1) heart sound (HS) is associated with closure of the mitral valve but as the valve leaflets are tissue thin, other mechanical factors associated with the closure of the valve are believed to account for the audible sounds. These include the oscillation of blood in the ventricular chambers, vibration of the chamber walls, abrupt tensing of the chordae tendinae supporting the mitral valve leaflets and tensing of the mitral valve itself. A second (S2) heart sound is associated with closure of the aortic and pulmonic valves. Commonly, two distinct components of the second sound are audible with the aortic component preceding the pulmonic component in a normal heart. The cause of the sound is not the valve leaflets coming together. Rather, it is due to the sudden deceleration of backward blood flow after ventricular contraction has ended and stretching of the aortic and pulmonic walls by the attempted backward flow of blood. Normally, the aortic component precedes the pulmonic component. The two components may move further apart during inspiration and closer together during exhalation. When there is a delayed activation of the left ventricle as may occur with an intraventricular conduction abnormality such as left bundle branch block, the aortic component may follow the pulmonic component with S2 becoming single during inspiration and widely split during exhalation. Correlating with overall cardiac function are heart sounds in the absence of primary valve abnormalities. The intensity of S1 may vary with the AV delay as well as with the vigor of contraction. The timing of S2 may also vary with contractility and the relative coordination or lack of coordination of cardiac contraction.

To implement internal detection of heart sounds using a pacemaker or ICD, acceleration signals detected by an on-board accelerometer can be processed to derive heart sound signals. One exemplary technique for deriving heart sounds using an accelerometer of an implanted device is discussed in U.S. Pat. No. 5,935,081 to Kadhiresan. More specifically, in the technique of Kadhiresan, the accelerometer signal is filtered using a band-pass filter to derive heart sounds. However, high frequency heart noises due to rapid turbulent flow are not detected. Moreover, the heart sounds appears to be derived only for diagnostic purposes, i.e. heart sound data is merely transmitted to an external device for subsequent review. Although the filter-based technique of Kadhiresan may be effective for recording certain types of heart sound data for diagnostic purposes, it does not provide for the on-board evaluation of overall cardiac function or for the automatic adjustment of pacing control parameters to permit ventricular resynchronization therapy. Moreover, by filtering out noises associated with turbulent flow, the technique does not permit detection of heart murmurs and the like, which can be important in determination of appropriate therapy.

Another exemplary technique for deriving heart sounds using an accelerometer is discussed in U.S. Pat. No. 5,836,987 to Baumann et al. Although the technique of Baumann et al. provides for automatic adjustment of certain pacing parameters (such as AV intervals) based on heart sound signals, it does not appear to provide for ventricular resynchronization therapy. Also, although Baumann et al. discuss the adjustment of certain pacing parameters so as to optimize cardiac performance, the technique does not appear to provide any capability for actually evaluating overall cardiac output in terms of, e.g., stroke volume, cardiac output, or max dP/dt. Hence, overall cardiac function is not actually tracked and optimization of pacing parameters based on overall cardiac function is not achieved.

Accordingly, it would be desirable provide improved techniques for use with implantable devices that permit the detection of heart sounds and heart murmurs, that provide for evaluation of overall cardiac function particularly in terms of stroke volume, cardiac output, or max dP/dt, and that permit optimization of pacing control parameters to maximize overall cardiac output and not just individual heart sound parameters. Additional aspects of the invention are directed to those ends.

SUMMARY

In accordance with a first aspect of the invention, a technique is provided for performing an evaluation of heart sounds using an implantable medical device wherein heart sound signals are detected and then parameters representative of overall cardiac function are automatically derived based on these signals. In an exemplary embodiment, the parameters include one or more of stroke volume, cardiac output, and max dP/dt. The heart sound signals are derived from acceleration signals provided by an accelerometer. Internal electrocardiographic signals are simultaneously sensed using electrodes within the heart of the patient. The heart sound signals and the electrocardiographic signals are analyzed to detect the S1 and S2 heart sounds and to identify the ejection period and, assuming no systolic regurgitant murmurs are present, the isovolumic (ISOV) interval. S1 and S2 heart sounds, the ejection period and the ISOV interval (if applicable) are then used to derive "predictors" for max dP/dt, stroke volume and cardiac output, i.e. values that vary along with changes in max dP/dt, stroke volume and cardiac output and hence can be used as a proxy for cardiac function. With the use of calibrated conversion factors, the predictor values can be converted, if desired, to scaled values representative of actual max dP/dt, stroke volume, and cardiac output, which may be stored for subsequent physician review.

In one specific example, assuming no systolic regurgitant murmurs have been detected, the ISOV interval is detected based on the duration of the S1 signal. Then, a predictor for max dP/dt is derived from a maximum amplitude of the S1 signal (S1_max) and the ISOV interval as follows:

$$P\_max\_dP/dt = S1\_max/ISOV.$$

Alternatively, the predictor for max dP/dt is represented using:

$$P\_max\_dP/dt = 80 \text{ mm Hg}/ISOV$$

A predictor for stroke volume (SV) is derived by approximating an integral of aortic flow over the ejection period using a linear function for the first one third of the ejection period and a quadratic function for the last two thirds, permitting the predictor for stroke volume to be represented using:

$$P\_SV = 11/18 * EJT\_prd * S1\_max/ISOV$$

A predictor for cardiac output (CO) is derived from the stroke volume and the heart rate as follows:

$$P\_CO = P\_SV * \text{heart rate}.$$

If systolic regurgitant murmurs are present in the ejection period, then ISOV is not evaluated and the predictor for max dP/dt is instead derived from:

$$P\_max\_dP/dt = S1\_max.$$

The predictor for stroke volume is instead estimated as:

$$P\_SV = 11/18 * EJT\_prd * S1\_max.$$

The predictor for cardiac output is again derived by multiplying stroke volume and the heart rate.

The predictor values vary in accordance with changes in actual cardiac function and hence are effective as bases for adjusting pacing parameters to optimize overall cardiac function. Changes in the predictors for cardiac function are also useful as a means for tracking progression of heart failure. Contractility is proportional to max dP/dt and so P_max_dP/dt also serves as a predictor or proxy for contractility.

In accordance with a second aspect of the invention, a technique is provided for performing heart sound monitoring using an implantable cardiac pacing device wherein heart sound signals are detected, parameters representative of overall cardiac function are evaluated and then control parameters are automatically adjusted based on the cardiac function parameters. In an exemplary embodiment, control parameters are adjusted to optimize cardiac function as represented by one or more predictors of stroke volume, cardiac output, and max dP/dt, which are derived from the heart sound signals using the techniques summarized above. Adjustments are triggered following any significant change in max dP/dt, stroke volume or cardiac output. Changes can also be triggered be significant changes in atrioventricular conduction interval, interventricular conduction interval, heart rate, orthostatic position, and exercise or activity state. Adjustments are preferably performed periodically even if no significant changes occur in the aforementioned values.

In accordance with a third aspect of the invention, a technique is provided for performing heart sound monitoring using an implantable biventricular cardiac pacing device wherein heart sound signals are detected and then biventricular pacing control parameters are automatically adjusted based on the heart sound signals. In an exemplary embodiment, parameters representative of overall cardiac function are first derived from the heart sound signals using the techniques summarized above, then biventricular pacing delay values are automatically adjusted based on the parameters so as to provide ventricular resynchronization therapy. In other examples, four chamber pacing parameters or multi-site pacing parameters are automatically adjusted.

Accordingly, improved techniques are provided for use within an implantable device for analyzing internal heart sound signals to derive parameters representative of overall cardiac function and for automatically adjusting pacing control parameters. Other features, objects and advantages are provided as well. System and method implementations of this techniques are set forth.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Stimulation Device

Figure 1:
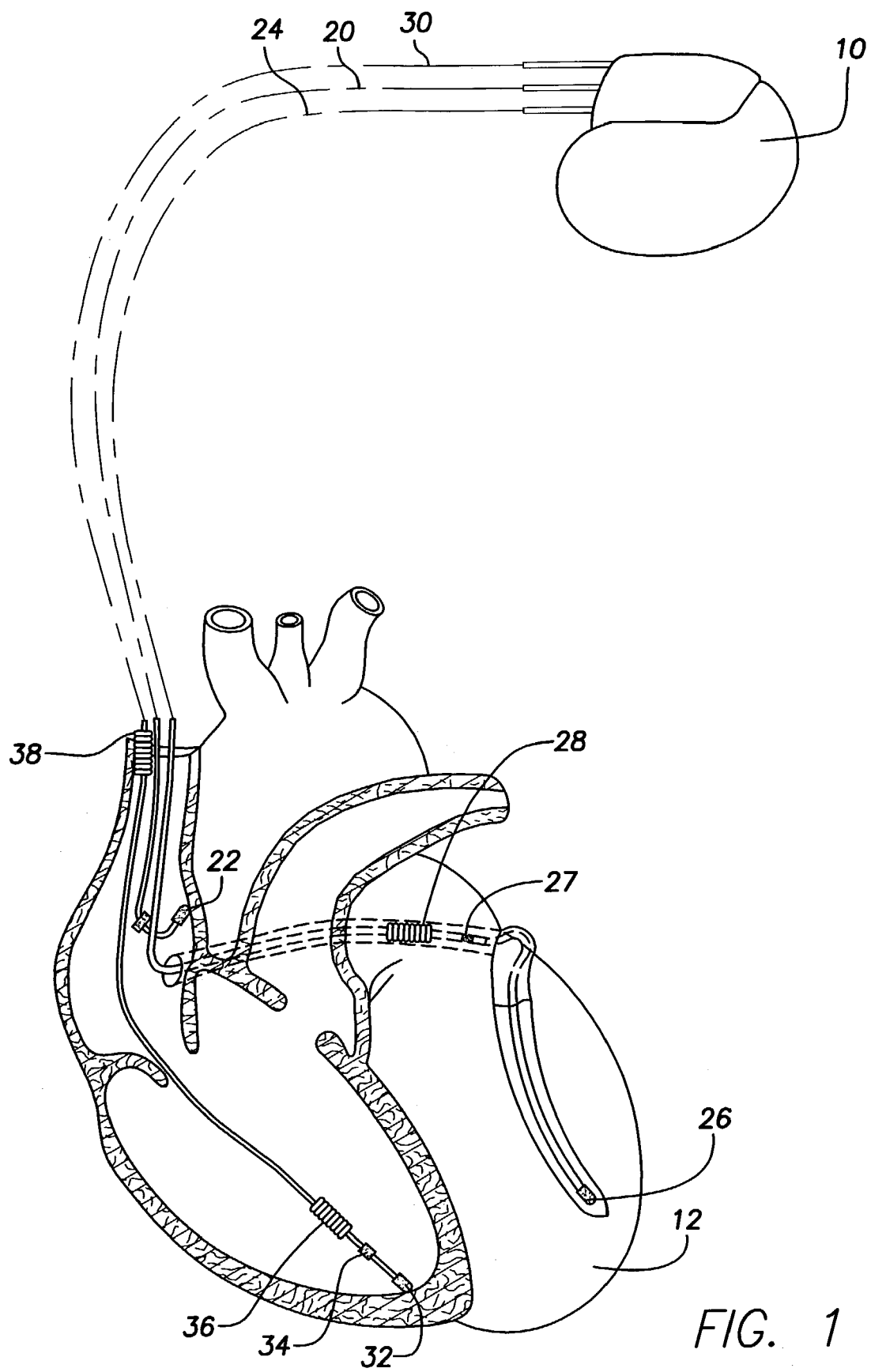
FIG. 1 is a simplified, partly cutaway view illustrating an implantable stimulation device in electrical communication with at least three leads implanted into the heart of a patient for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
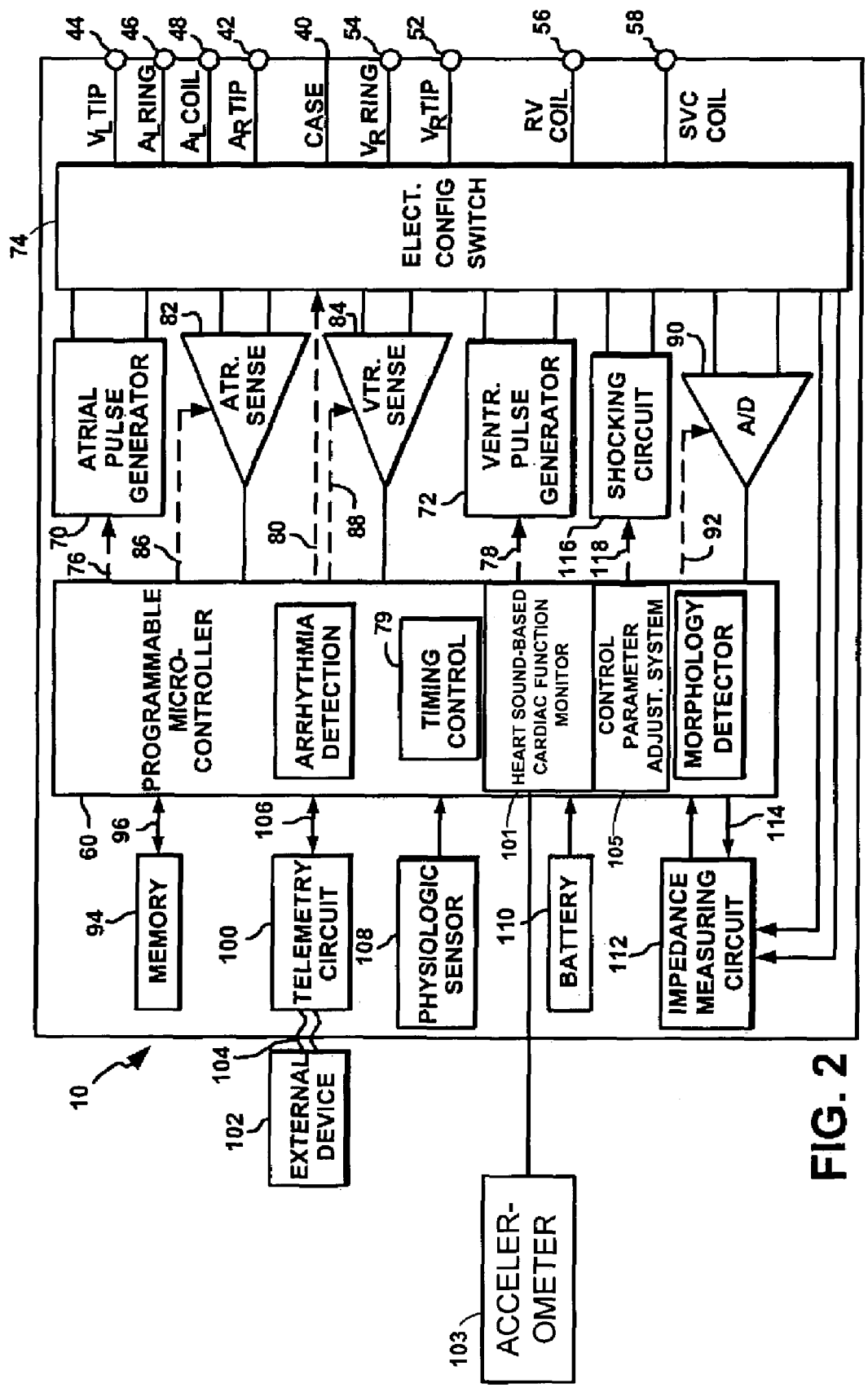
FIG. 2 is a functional block diagram of the multi-chamber implantable stimulation device of FIG. 2, illustrating the basic elements that provide cardioversion, defibrillation and/or pacing stimulation in four chambers of the heart and particularly illustrating a heart sound-based cardiac function monitor for automatically evaluating the cardiac function of the patient and a control parameter adjustment system for automatically adjusting pacing parameters to optimize cardiac function.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber (s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Note that, strictly speaking, P-waves, R-waves and T-waves are features of the surface EKG. For convenience, herein, the terms P-wave, R-wave and T-wave are used to refer to the corresponding internal signal component.

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

The microcontroller also includes a heart sound-based cardiac function monitor 101, which converts signals received from an accelerometer 103 into heart sound signals, then determines cardiac function based on the heart sound signals in combination with internal electrical cardiac signals. Cardiac function is evaluated in terms of one or more of: max dP/dt, stroke volume, or cardiac output. The microcontroller also includes a control parameter adjustment system 105, which automatically adjusts pacing parameters, particularly ventricular synchronization parameters, for example, to improve cardiac function. The operation of monitor 101 and adjustment system 105 is described in greater detail below in connection with the FIGS. 3–7.

The accelerometer may be mounted within the can of the implanted device or mounted elsewhere within the body including at the distal ends of the leads. Implantable accelerometers, including lead-mounted accelerometers, are described in U.S. Pat. No. 6,002,963 to Mouchawar, et al., entitled "Multi-Axial Accelerometer-Based Sensor For An Implantable Medical Device And Method Of Measuring Motion Measurements Therefor", Dec. 14, 1999, and in U.S. Pat. No. 5,628,777 to Moberg, et al., entitled "Implantable Leads Incorporating Cardiac Wall Acceleration Sensors and Method of Fabrication", which are both incorporated by reference herein in their entirety.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 should preferably have a predictable discharge characteristic so that elective replacement time can be detected. Accordingly, the stimulation device 10 can employ lithium/silver vanadium oxide batteries or any other appropriate power source.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

Overview of the Heart Sound Technique

Figure 3:
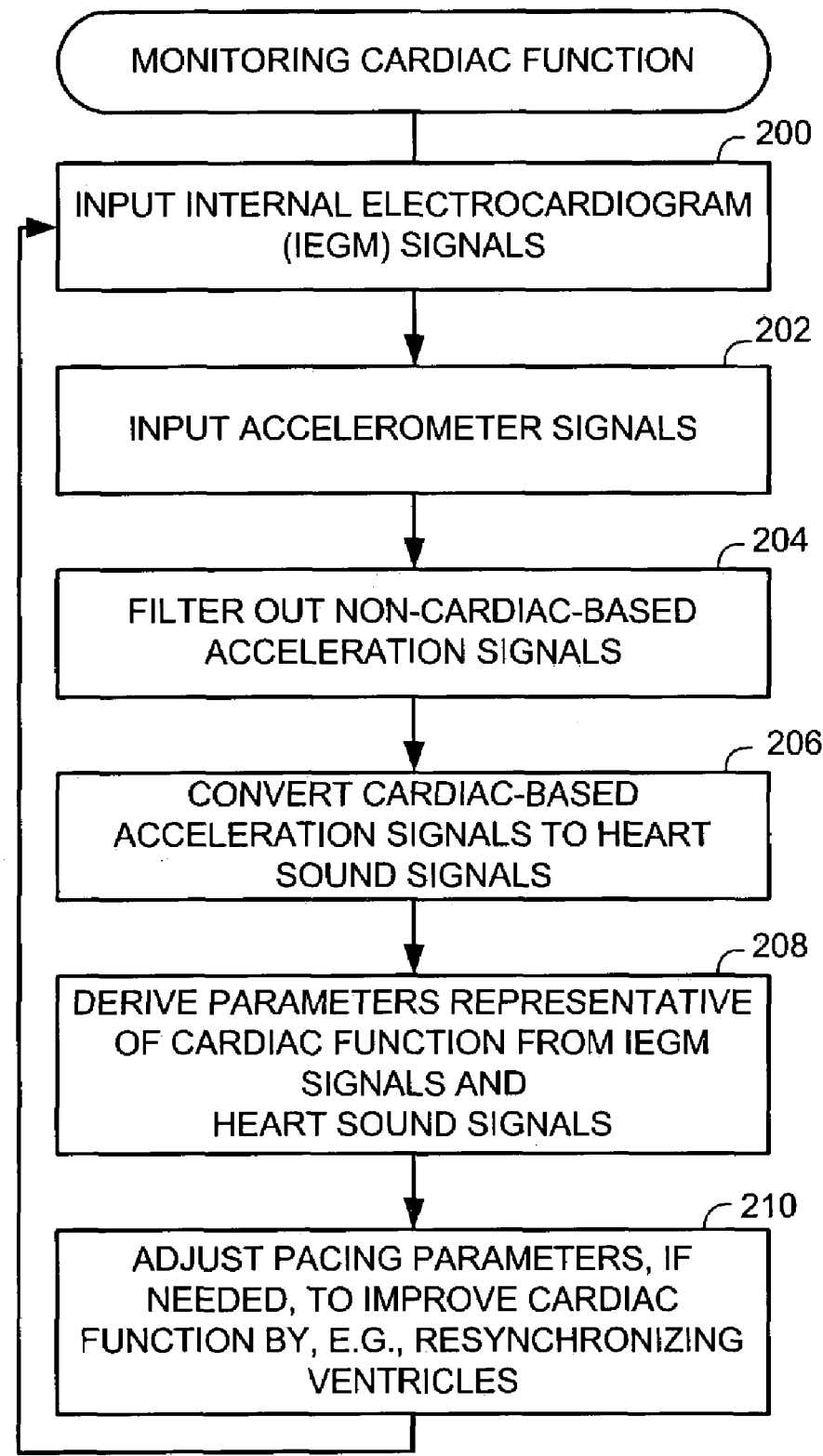
FIG. 3 is a flow diagram providing an overview of a method performed by the implantable device of FIG. 2 for monitoring cardiac function based on the heart sounds and for adjusting pacing parameters in response thereto.

Referring now to FIG. 3, the operation of cardiac function monitor 101 and control parameter adjustment system 105 of FIG. 2 will be described. Initially, a step 200, the cardiac function monitor inputs internal electrocardiographic signals, also referred to herein as intracardiac electrogram (IEGM) signals. At step 202, accelerometer signals (typically represented in terms of three-dimensional orthogonal acceleration values) are input from accelerometer 103 (also FIG. 2). The accelerometer signals, which vary with time, represent not only changes in the orientation and motion of the patient but also vibration of internal tissues surrounding the accelerometer caused by sounds emanating from the heart. In other words, the accelerometer signals also represent the cardiac sounds, including the S1 and S2 heart sounds as well as any heart valve regurgitation noises. At step 204, the cardiac function monitor filters out all non-cardiac-based acceleration signals, i.e. the monitor filters out all signals not corresponding to heart sounds and murmurs. This may be achieved, for example, using otherwise conventional signal filtering techniques adapted to filter out all signals not substantially consistent with those expected to rise in connection with heart sounds and murmurs. Filtering may be performed by components of the cardiac function monitor itself or by a separate filter provided within the implanted device 10 (not separately shown). Heart sounds are typically below 300 Hz with S1 and S2 around 50–60 Hz. In one example, a filter having a bandwidth of 1 to 7 Hz is employed. In other examples, filters with bandwidths up to 60 Hz are employed. At step 206, the filtered acceleration signals are then converted to heart sound signals. Information regarding techniques for extracting heart sound signals from accelerometer signals is provided in "*Accelerometer Type Cardiac Transducer for Detection of Low-Level Heart Sounds*" by Padmanabhan et al., IEEE Trans. Biomed. Eng., 1993 January; 40(1):21–28, and in various of the patents incorporated above. Information regarding filtering techniques for filtering accelerometer-based signals to obtain parameters indicative of heart beat is provided in U.S. Pat. No. 5,991,661 to Park et al., entitled "System and Method for Measuring Cardiac Activity", which is also incorporated by reference herein.

At step 208, the monitoring unit then derives parameters representative of cardiac function (e.g. predictors for max dP/dt, stroke volume and cardiac output) by analyzing the heart sound signals in combination with the IEGM signals. Briefly, the IEGM signals are analyzed to determine the current heart rate and to identify internal signals corresponding to R-waves and T-waves. Exemplary R-waves and T-waves are shown within a surface electrocardiogram graph 211 of FIG. 4. Note that the shape of the IEGM signals processed by the implanted device may differ from the surface electrocardiogram 211. The internal R-waves and T-waves are then used to facilitate identifying the S1 and S2 heart sounds from within the heart sound signals. Exemplary S1 and S2 heart sounds are shown within heart sound signal graph 213 of FIG. 4. The sources of the S1 and S2 heart sounds are described above.

Figure 4:
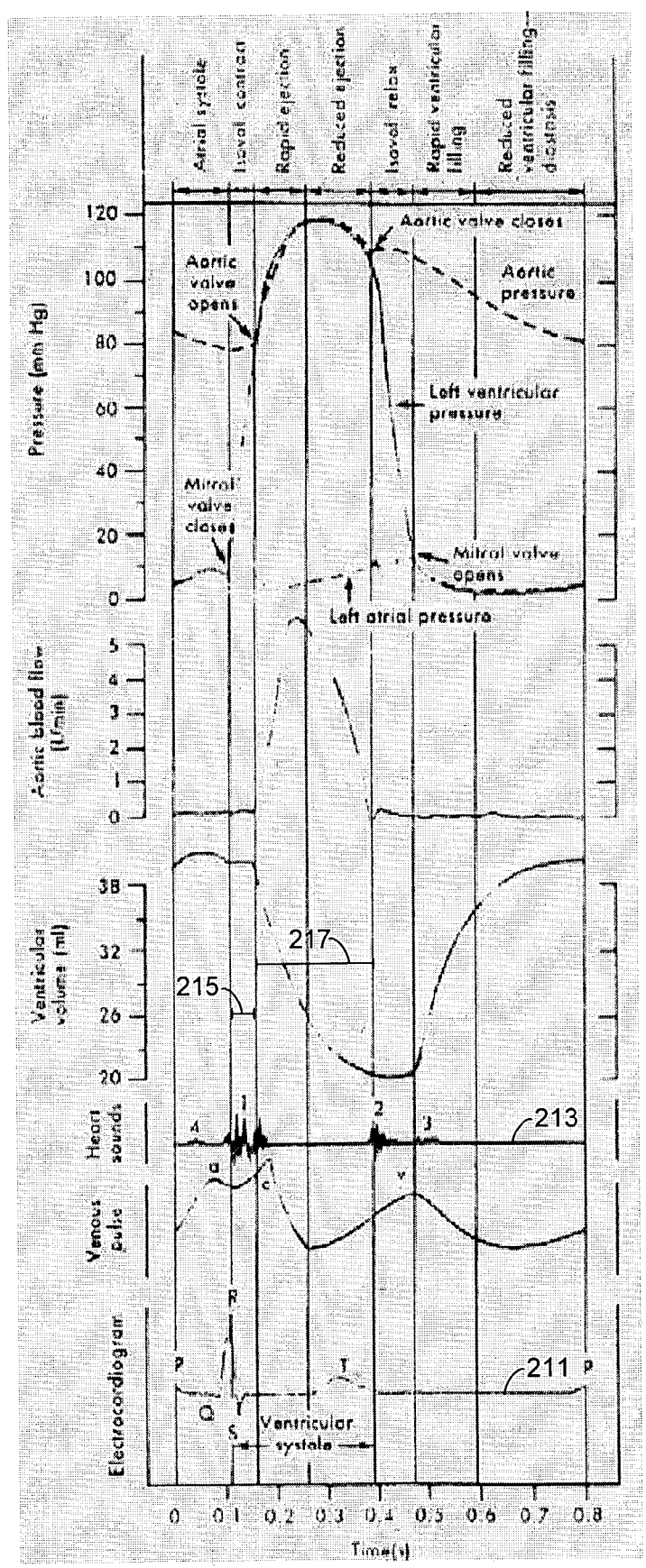
FIG. 4 is graph illustrating exemplary heart sounds and electrical cardiac signals along with corresponding charts of left ventricular, left atrial and aortic pressures, arterial and venous pulse pressures and ventricular volume.

The duration of the S1 heart sound is used to determine the ISOV interval (interval 215 of FIG. 4.) During the ISOV interval, left ventricular pressure abruptly increases as a result of the contraction of the heart. The contraction is referred to as isovolumic because the valves between the ventricles and the atria (as well as between the ventricles and the arterial circulation) remain closed during the contraction. Thus, no blood is ejected from the ventricles and so the ventricles hold the same volume. The ISOV interval begins with the closing of the atrio-ventricular valves and ends with the opening of the pulmonary and aortic valves. The ISOV interval is preceded by atrial systole and followed by a rapid ejection phase. The interval between the S1 and S2 heart sounds is used to determine the ejection period (interval 217 of FIG. 4.), which represents the interval between opening and closing of the aortic valve. Max dP/dt is then derived during step 208 from the ISOV interval. The stroke volume is derived from the ejection period in combination with a peak to peak maximum of the S1 heart sounds signal and the ISOV interval. Cardiac output is derived from the stroke volume and the heart rate. Heart murmurs are also detected and, if present, max dP/dt and stroke volume are derived without using ISOV. This is all described in greater detail below with reference to FIG. 5.

At step 210, the adjustment system automatically adjusts pacing parameters, if needed, in an effort to improve or optimize cardiac function (typically via resynchronization of the ventricles.) Preferably, the adjustment unit also verifies that the adjusted parameters succeeded in actually achieving improvement in cardiac function. Preferably, cardiac function is monitored using the technique of FIG. 3 more or less continuously and adjustments are made to the pacing parameters whenever a significant change within overall cardiac function (or within one of the parameters representative of cardiac function such as stroke volume) is detected. Additional factors for triggering adjustment to pacing parameters are discussed below in connection with FIG. 6. An exemplary technique for performing the actual adjustments so as to optimize cardiac function is described in below with reference to FIG. 7. Note that the optimal pacing parameter settings identified for use when the patient is at rest or sleeping may differ markedly from those used during a period of vigorous physical activity or when awake but not very active.

Thus, FIG. 3, provides an overview of a technique for automatically evaluating parameters representative of cardiac function performed by an implantable medical device. No external heart sound monitoring system is required. Rather, heart sound signals are derived from accelerometer signals. Hence, changes in cardiac function can be detected without requiring office visits with the physician. Moreover, pacing parameters are automatically adjusted so as to optimize cardiac function. In this regard, otherwise ventricular resynchronization techniques may be employed within biventricular pacing systems so as to provide proper synchronization of ventricles. Improved cardiac function is achieved and the risk of ventricular tachyarrhythmias is substantially reduced.

Exemplary Cardiac Function Parameter Estimation Technique

Figure 5:
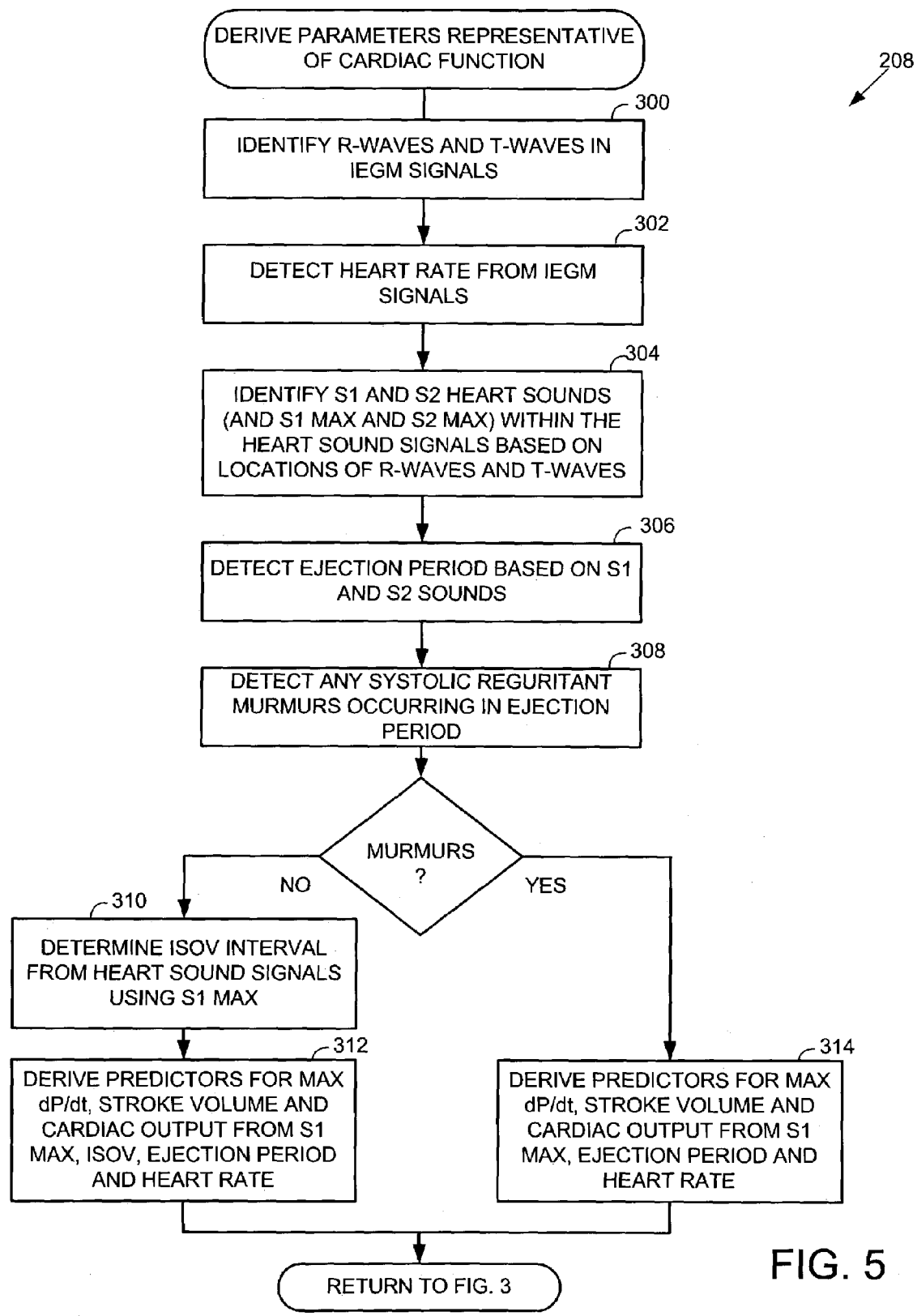
FIG. 5 is a flow diagram illustrating an exemplary method for deriving parameters representative of cardiac function (particularly in max dP/dt, stroke volume and cardiac output) for use with the technique of FIG. 3.

Referring to FIG. 5, the technique of step 208 for deriving parameters representative of cardiac function is described in greater detail specifically with reference to the derivation of predictors for max dP/dt, stroke volume and cardiac output. Beginning at step 300, if the cardiac function monitor has not done so, the monitor identifies ventricular depolarization signals (i.e. internal versions of R-waves) and ventricular repolarization signals (i.e. internal versions of T-waves) within the input IEGM signals. R-waves and T-waves can be located by the peak detection methods or running time average methods. At step 302, the monitor detects the heart rate of the patient based on the IEGM signals. The heart rate may be detected in accordance with conventional techniques by monitoring the time interval between consecutive intrinsic R-waves or V-pulses.

At step 304, the monitor uses the locations of the R-waves and T-waves to define search windows for detecting the S1 and S2 heart sounds within the heart sound signal. In one example, the monitor initiates an S1 search window at the peak of an R-wave with a search window duration (or width) set to $\alpha$*(T-wave peak to R-wave peak) where $\alpha$=0.8 to 1.0. For patients known to have AV valvular regurgitation, $\alpha$ may instead be set to a smaller value (e.g. 0.5). The monitor then initiates an S2 search window at the T-wave peak with the window set to end 200 ms after T-wave peak. Within the S1 window, the monitor rectifies the heart sound signal to yield a "rec_S1" signal and then detects the maximum of the rectified signal (referred to herein as "rec_S1_max".) Based on rec_S1_max, an S1 threshold (also referred to herein as "$S1_{threshold}$") is set based on a pre-determined S1 percentage of, for example, 60%. The monitor then determines when the rec_S1 signal exceeds $S1_{threshold}$. The first point at which rec_S1 exceeds $S1_{threshold}$ after the peak of the R-wave defines the onset of S1 (also referred to herein as "S1_t0"). The last point at which rec_S1 falls below S1 threshold defines the end of S1 (also referred to herein as "S1_t1"). Similarly, following the peak of the T-wave, the monitor detects S2_t0 and S2_t1 by rectifying the heart sound signal within the S2 search window to yield rec_S2 and then comparing rec_S2 against an S2 threshold (referred to herein as "$S2_{threshold}$") calculated based on a percentage (e.g., 60%) of a rec_S2_max value. (The percentages used for defining the S1 and S2 thresholds need not be the same.) Thus, the beginning and end of the S1 and S2 heart sounds are detected based on when the rectified heart sound exceeds or falls below certain threshold values set based in the maxima of the rectified signal. Alternatively, the rectified signal may be integrated to determining the total energy in the signal, which is then used as a basis to set threshold values. Other techniques may be employed as well.

At step 304, the monitor also detects the peak to peak maximum of the unrectified S1 and S2 heart signals (referred to herein as "S1_max" and "S2_max", respectively) and determines the location of S1_max and S2_max, i.e. the points in time when S1_max and S2_max occur, referred to herein as "S1_max_time" and "S2_max_time". In addition, the monitor calculates the interval between S1 and S2 (also referred to herein as the "S1_S2") based on S1_max_time and S2_max_time wherein:

$$S1\_S2 = S1\_max\_time - S2\_max\_time.$$

Note that the peak-to-peak maxima of S1 and S2 (S1_max and S2_max) will likely differ from the maxima of the rectified signals (rec_S2_max and rec_S2_max). S1_max and S2_max are calculated by detecting the maximum difference between the positive and negative heart sound signals within the respective search window; whereas rec_S2_max and rec_S2_max are calculated by detecting the maximum of the rectified signal, which is always positive.

At step 306, monitor detects the beginning and the end of the ejection period based upon the S1 and S2 heart sounds. The ejection period (also referred to herein as "EJT_prd") generally represents the time interval from when the aortic valve opens to when aortic valve closes and is approximately equal to the time period from the end of S1 to the onset of S2:

$$EJT\_prd = (S2\_t0 - S1\_t1)$$

Then, at step 308, the monitor determines whether any systolic regurgitant murmurs have occurred during the ejection period. To detect such murmurs, the monitor employs a window-based technique similar to the one used for detecting S1 and S2. More specifically, the monitor searches for murmurs during a murmur detection interval from (S1_max_time+0.5*(1−x)*S1_S2 interval) to (S2_max_time−0.5*(1−x)*S1_S2 interval), where x is a murmur window scaling value pre-set to, for example, 0.6 or 0.7. Note that, if x is set to 1, the murmur detection window has a duration of S1_S2 and extends from S1_max_time to S2_max_time. If x is set to 0, the murmur detection window is of zero length. By setting x in the range of 0.6 to 0.7, a murmur detection window is thereby provided that begins sometime after the end of S1 and commences sometime before S2 thus excluding the S1 and S2 heart sounds. In any case, the monitor determines the peak to peak maximum of the heart sound signal during the murmur detection interval and compares it to a pre-determined murmur detection threshold and, if it exceeds the murmur detection threshold, the monitor thereby concludes that murmurs are present. More specifically, within the murmur detection window, the monitor rectifies the heart sound signal to yield a rec_murmer signal and then detects the maximum of the rectified signal (referred to herein as "rec_murmer_max"). Based on rec_murmer_max, a murmur amplitude threshold (also referred to herein as "$murmer_{threshold}$") is set based on a pre-determined murmur threshold percentage value of, for example, 60%. The monitor then determines whether rec_murmer_max exceeds $murmer_{threshold}$ and, if so, murmurs are thereby deemed to be present and the conclusion is drawn that the patient has heart valve regurgitation. Otherwise, murmurs are not present and the patient is not deemed to have heart valve regurgitation.

Thereafter, processing depends upon whether systolic regurgitant murmurs have been detected. If such murmurs have not been detected then, at step 310, the monitor determines the ISOV interval using based on the duration of S1 by calculating:

$$ISOV = S1\_t1 - S1\_t0$$

At step 312, the monitor develops predictors for maximum dP/dt, stroke volume and cardiac output based upon S1_max, ISOV interval, the ejection period and the current heart rate. As noted above, the predictors are values that vary with the corresponding cardiac function parameter (such as max dP/dt) and hence are useful as proxies for cardiac function. The use of the "predictor" herein is not meant to imply that future values for these parameters are predicted.

The predictor for max dP/dt is calculated as follows:

$$P\_max\_dP/dt = S1\_max / ISOV.$$

The predictor for max dP/dt is based on the idea that maximum of dP/dt is proportional to the peak of aortic blood flow and that the peak of the aortic flow is proportional to S1_max/ISOV. In this regard, if the S1 heart sound is particularly loud (i.e. S1_max is large), that is an indication that the aortic flow had been significant (since the S1 sound is largely due to the sudden stoppage of the aortic flow caused by closure of the mitral and tricuspid valves.) Hence, a loud S1 indicates a high aortic flow, which indicates a large volume of blood pumped into the ventricle. Thus, S1_max provides an indication of the amount of blood in the ventricle. During the ISOV interval, the ventricle contracts thereby raising the pressure of the blood therein and providing for a change in pressure as a function of time (i.e. dP/dt.) The pressure increases until it reaches a threshold, typically a pressure equal to 80 mm Hg, marking the end of the ISOV interval, at which point the aortic valve is opened and the blood is pumped out of the ventricle. Hence, the shorter the ISOV interval, the faster the pressure increases in the ventricle and hence the higher the maximum of dP/dt. Thus, max dP/dt is related to both S1_max and to the duration of the ISOV interval and can be estimated based on the ratio of S1_max to the duration of the ISOV interval.

Alternately, the predictor for maximum dP/dt may be calculated using:

$$P\_max\_dP/dt = 80 \text{ mm Hg}/ISOV.$$

As noted, pressure increases in the ventricle during the ISOV interval until a triggering threshold (typically 80 mm Hg) is reached. The pressure is near zero at the beginning of the ISOV interval and hence the average dP/dt is approximately equal to the threshold pressure/ISOV. In addition, the change is pressure is fairly uniform during the ISOV interval and so the max dP/dt is approximately the same as the average dP/dt. Thus, max dP/dt can be estimated based on ISOV interval and the triggering threshold of 80 mm Hg.

Hence, two techniques are provided for deriving a predictor for max dP/dt. Depending upon the implementation, either one or the other or a combination of the two may be used. For example, the monitor may be configured to separately calculate P_max_dP/dt using both formulas, then average the results. In other implementations, following implantation, max dP/dt is calculated using external heart sound monitoring techniques and compared against estimates simultaneously generated by the implanted device using the two formulas. The formula that more closely tracks the value detected using the external technique is then selected and control signals are transmitted from an external programmer to the implanted device for controlling the device to use the selected formula. Note also that contractility is proportional to dP/dt and so P_max_dP/dt also serves as a predictor or proxy for contractility.

Next, the monitor calculates a predictor (P_SV) for stroke volume based on ejection period, S1_max and ISOV using:

$$P\_SV = 11/18 * EJT\_prd * S1\_max/ISOV.$$

This approximation of the stroke volume is derived as follows. Stroke volume (SV) is derived from the aortic flow as a function of time (i.e. Aortic_flow(t)) using:

$$SV = \int Aortic\_flow(t) dt$$

wherein the integration is performed over the ejection period, i.e. from t=S1_t1 to t=S2_t0.

However, the integral of the aortic flow as a function of time may be approximated using a linear function for the first one third of the ejection period and a quadratic function for the last two thirds. The approximated aortic flow function is:

$$Aortic\_flow(t) \approx Aortic\_flow\_max * t/(1/3 * EJT\_prd)$$

for $0 \leq t \leq 1/3$ EJT_prd and $$Aortic\_flow(t) \approx Aortic\_flow\_max * [1-(t^2 - 2/3 EJT\_prd * t + (EJT\_prd/3)^2)/(2/3 * EJT\_prd)^2]$$

for $1/3$ EJT_prd $\leq t \leq$ EJT_prd where Aortic_flow_max≈S1_max/ISOV.
Hence:

$$\int Aortic\_flow(t) dt \approx [1/2 * Aortic\_flow\_max * EJT\_prd/3)] + [4/3 * Aortic\_flow\_max * EJT\_prd/3] = 11/18 * EJT\_prd * S1\_max/ISOV$$

yielding the equation for P_SV above.

Finally, cardiac output is stroke volume multiplied by heart rate. Hence, a predictor for cardiac output may be calculated from the predicator for stroke volume using:

$$P\_CO = P\_SV * HR$$

or $$P\_CO = 11/18 * EJT\_prd * S1\_max/ISOV * HR.$$

If, however, systolic regurgitant murmurs had been detected during ejection period, then step 314 is instead performed wherein the monitor derives predictors for max dP/dt, stroke volume and cardiac output based upon the S1_max, the ejection period and the current heart rate. In other words, ISOV interval is no longer used in the estimation. ISOV interval is not employed because it cannot easily be determined based on S1 due to the presence of the murmurs. More specifically, the predictors used if systolic regurgitant murmurs are present are:

$$P\_max\_dP/dt = S1\_max$$

$$P\_SV = 11/18 * EJT\_prd * S1\_max$$

and $$P\_CO = 11/18 * EJT\_prd * S1\_max * HR.$$

Note that the alternate formula for P_max_dP/dt of 80 mm Hg/ISOV is not used since ISOV is not calculated. For the murmur-based equations, ISOV is essentially approximated as "1" and so the predictor values for use with murmurs may differ significantly in magnitude from those for use without murmurs. Hence, for a given patient, either the murmur-based equations or the non-murmur based equations (but not both) are used depending up whether heart value regurgitation is detected. In any case, following either step 312 or step 314, processing returns to FIG. 3.

For patients known to have heart valve regurgitation, the value for α used in step 304 may instead be set to a smaller value (e.g. 0.5) than otherwise. In other words, after murmurs are detected for the first time at step 308, the value for α may be reset for subsequent iterations of FIG. 5. In addition, for most patients with heart valve regurgitation, murmurs are typically always present. Hence, once heart valve regurgitation has been detected, the monitor need not seek to detect the murmurs at step 308 during each iteration of FIG. 5. Rather, the monitor may be programmed such that, once murmurs have been detected, step 308 is no longer performed (or is performed only occasionally to verified continued valve regurgitation). Also, note that, if the type of the accelerometer employed (or the filter employed) is not capable of detecting noises associated with murmurs, then murmur detection is not required and steps 310 and 312 are always employed.

Thus, various equations are provided for calculating predictors or proxies for cardiac function parameters (i.e. max dP/dt, SV or CO). The actual numerical magnitude of the predictors may be different significantly from the actual numerical magnitude of the corresponding cardiac function. Indeed, the units for the predictors do not necessarily match the units of the corresponding cardiac function parameter. For example, the units for the non-murmur based predictor for max dP/dt (P_max_dP/dt) is not in units of pressure/time. However, the predictors are nevertheless useful as proxies for cardiac function. Moreover, by using experimentally calculated conversion factors, calibrated for use with individual patients, the predictors can be converted to values properly scaled with the corresponding cardiac function. In this regard, during an initial calibration process following implant of the device, true values for the various cardiac function parameters are determined for the patient using external heart sound monitoring techniques while the predictor values are simultaneously calculated by the implanted device. Then conversion factors are calculated by an external programmer for scaling the predictor values to approximately match the cardiac function parameters. The conversion factors are transmitted to and stored within the implanted device, thereby permitting the device to continuously convert predictor values into estimates of actual cardiac function, scaled appropriately and with the correct units. This information is preferably stored in the implanted device for subsequent transmission to the external programmer during a follow-up session, to permit the physician to thereby access and review properly-scaled estimates of cardiac function.

Hence, FIG. 5 provides an example of one technique for calculating predictors for max dP/dt, stroke volume and cardiac output using accelerometer-based heart sound signals and IEGM signals. Other techniques may alternatively be employed. For example, rather than estimating aortic flow by a linear function in the first third of the ejection period and by a quadratic equation in the last two thirds, different or more precise formulas may be employed. As another example, linear formulas may be used in both the first third and the last third of the ejection period, although this results in a somewhat less accurate predictor of stroke volume. Alternatively, a more precise polynomial function may be fitted to the first third of the ejection period to replace the linear function or a more precise polynomial function maybe fitted to the entire ejection period. In addition, if individual values for aortic_flow(t) are available throughout the entire ejection period, then stroke volume may be derived by directly integrating aortic_flow(t) over the ejection period. The exemplary formulas provided above for representing the aortic flow are preferred as it is believed the formulas provide a sufficiently accurate approximation of the aortic flow while permitting stroke volume to be easily calculated.

Depending upon the implementation, all three predictors (i.e. max dP/dt, SV or CO) need not be derived. Rather, in some implementations, only a single predictor (e.g. stroke volume) is used. In addition, predictors for other cardiac function parameters, such as end-diastolic volume, end-systolic volume, ejection fraction or cardiac output index, may be alternatively or additionally evaluated in accordance with the general principles of the invention.

Exemplary Adjustment Triggering Technique

Figure 6:
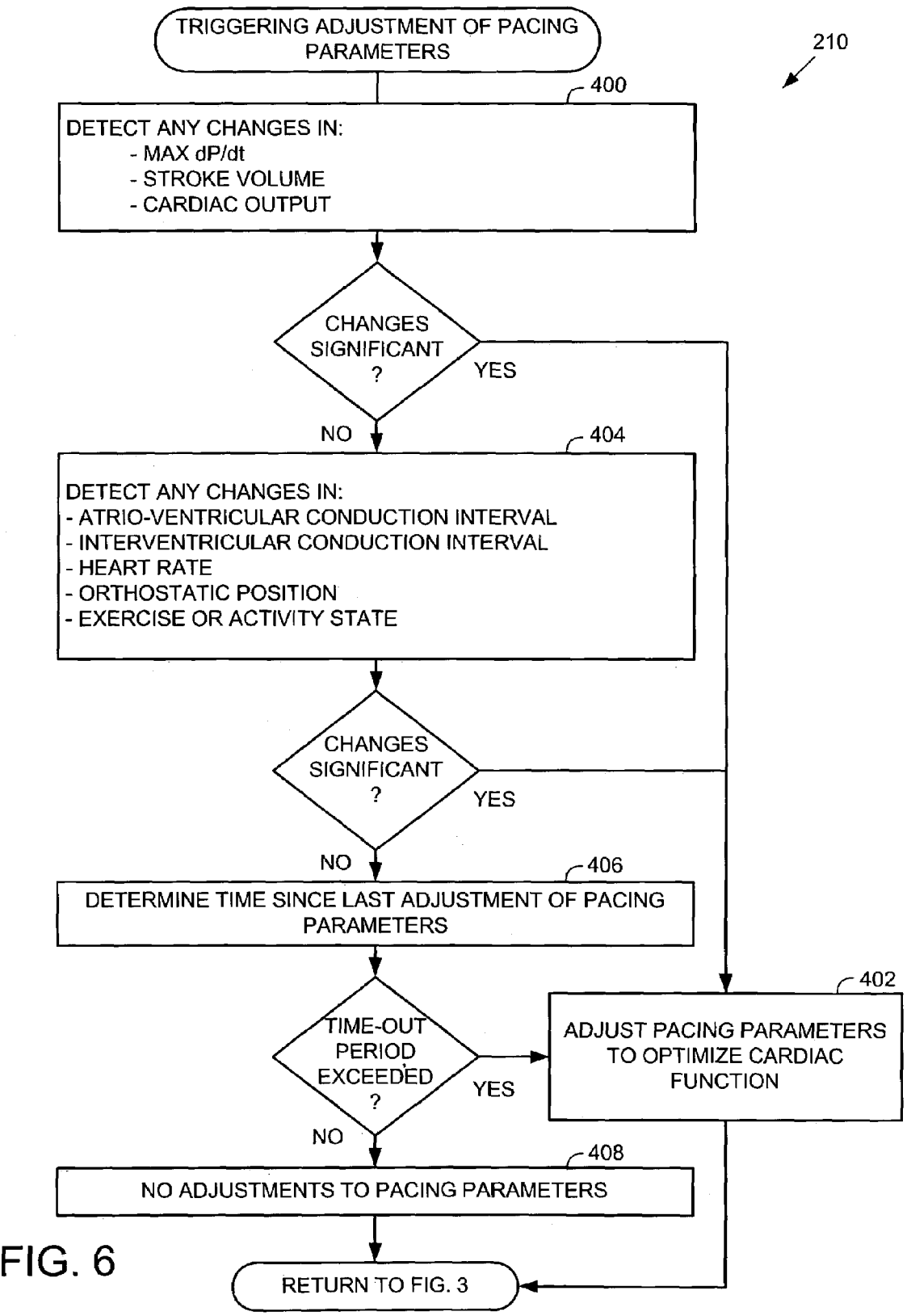
FIG. 6 is a flow diagram illustrating an exemplary method for triggering of automatic adjustment of cardiac pacing parameters for use with the technique of FIG. 5.

Referring now to FIG. 6, exemplary techniques for determining whether to trigger an adjustment of pacing parameters as part of step 210 of FIG. 5 will now be described. The steps of FIG. 6 are performed by control parameter adjustment system 105 (FIG. 2). First, at step 400, the adjustment system determines whether any significant changes have recently occurred within the cardiac function parameters (i.e. within the predictors for max dP/dt, stroke volume or cardiac output.) To this end, the adjustment system stores the various values representing cardiac function detected by the monitor and compares the most recent values with previously stored values. As part of step 400, the individual cardiac function parameters may be combined to yield a single value representative of overall cardiac function. For example, the individual max dP/dt, stroke volume and cardiac output values may be averaged to yield a single cardiac function "metric". The values are also stored so as to provide a diagnostic record of cardiac function for the patient for subsequent review by a physician.

If any significant changes occur in any one of the cardiac function parameters, step 402 is performed wherein the adjustment system adjusts pacing parameters so as to improve (and preferably optimize) cardiac function. Note that, insofar as cardiac output is a function of stroke volume and heart rate, significant changes in heart rate can directly affect cardiac output, thereby triggering the optimization step. Significant changes in overall cardiac function (or in any of the individual cardiac function parameters) may be indicative of the progression or repression of heart failure. If so equipped, the implanted device may also transmit warning signals to an external warning device (such as a bedside monitor) if significant adverse changes in cardiac function are detected to thereby immediately warn the patient.

Even if no significant changes have been detected within the cardiac function parameters, at step 404, the adjustment system determines whether any significant changes have occurred in: the atrioventricular conduction interval, the interventricular conduction interval, the heart rate, the orthostatic position of the patient, and the exercise or activity states of the patient. Assuming that any one of these parameters has changed significantly, pacing parameters are also adjusted at step 402. Depending upon the implementation, temporary changes in these parameters may be disregarded. For example, if the heart rate increases significantly but only for a short period of time, such as less than 1 minute, no changes in pacing parameters are performed. Also, insofar as heart rate is concerned, as noted above, a change in heart rate can trigger a change in cardiac output thus triggering an adjustment in pacing parameters following step 400. However, even if there is no net change in cardiac output, a change in heart rate alone may also trigger adjustment of the parameters following step 404.

Insofar as changes in orthostatic position are concerned, techniques for detecting the posture of the patient and for detecting changes in posture may be found in copending U.S. patent application Ser. No. 10/329,233, entitled "System And Method For Determining Patient Posture Based On 3-D Trajectory Using An Implantable Medical Device," of Koh et al., filed Dec. 23, 2002; U.S. patent application Ser. No. 10/328,642, entitled "System And Method For Determining Patient Posture Based On 3-D Trajectory Using An Implantable Medical Device," of Koh et al., filed Dec. 23, 2002; which are incorporated herein by reference.

Finally, even if no significant changes are detected at steps 400 and 404, pacing parameters are nevertheless adjusted periodically whenever a predetermined timeout value is exceeded at step 406. The timeout period maybe, for example, 15 minutes, 30 minutes, for other value programmed by the physician. If adjustment of the pacing parameters is not triggered following steps 400, 404, or 406, then no adjustments need to be performed (step 408) and processing simply returns to FIG. 3 for further processing.

Exemplary Pacing Parameter Adjustment Technique

Figure 7:
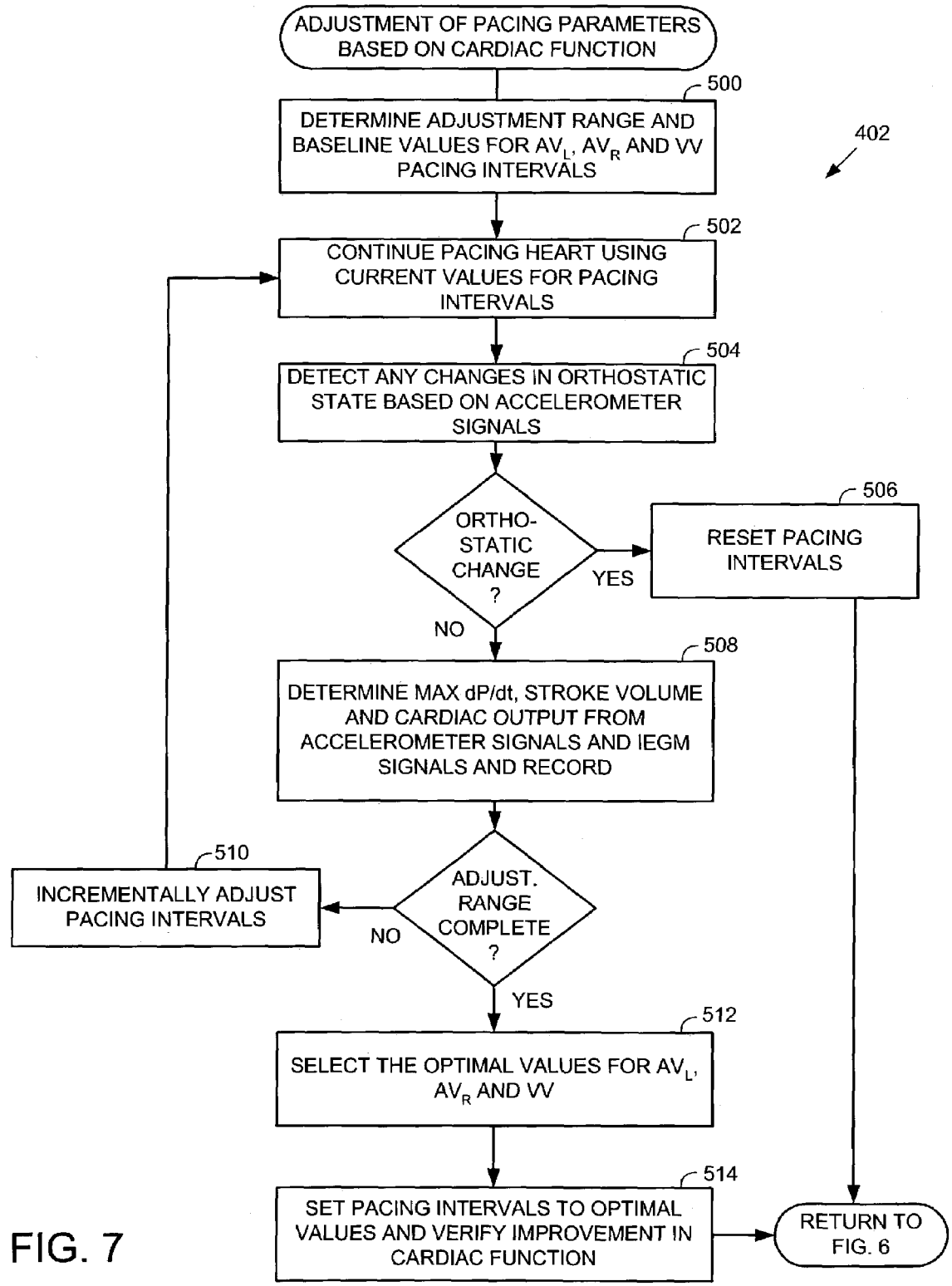
FIG. 7 is a flow diagram illustrating an exemplary method for adjusting cardiac pacing parameters so as to optimize cardiac function for use with the technique of FIG. 5.

Referring now to FIG. 7, exemplary techniques for adjusting pacing parameters (step 402 the FIG. 6) will now be described. In example of FIG. 7, a biventricular pacing system is assumed. The specific pacing parameters to be adjusted include the $AV_R$ and $AV_L$ and VV intervals (wherein $AV_R$ and $AV_L$ refer, respectively, to the AV interval on the right side and the AV interval on the left side during biventricular pacing if both RV and LV are independently programmable.) At step 500, the adjustment system inputs the latest values for these parameters and determines an adjustment range for use with each. The adjustment range maybe, for example, in the range of ±10% or ±20% of the current value. Alternatively, the adjustment system estimates optimal values for $AV_R$, $AV_L$ and VV using atrioventricular and interventricular conduction delays. The adjustment system then determines an adjustment range surrounding on the optimal values. Again, the adjustment range may be in the range of ±10% or ±20% of the optimal value. As will be described, the adjustment system incrementally varies each of these parameters through their respective adjustment range in an attempt to find the specific value achieving maximum overall cardiac function (or which maximizes one of the individual cardiac function parameters).

At step 500, the adjustment system also sets each of the parameters to be adjusted to one end of the range of adjustment values, typically the lower end, which represents a baseline value. At step 502, the adjustment system controls other components of the implanted device to pace using the adjusted values while, at step 504, the adjustment system monitors acceleration signals received from accelerometer to detect any changes in orthostatic position of the patient. If a change in orthostatic position is detected, the optimization process is aborted, at step 506, and the pacing parameters are returned to their pre-adjustment levels. Assuming that no changes in orthostatic position are detected then, at step 508, the adjustment system inputs the latest values for the cardiac function parameters from the monitoring unit and stores these values. The adjustment system also preferably calculates a metric value representative of some combination of the parameters. The metric value may represent, for example, a straight average of the three values.

In any case, at step 510, the adjustment system then incrementally adjusts one or more of the individual pacing values then returns to step 502 for continued pacing using the newly adjusted values. Steps 502 to 508 are repeated until the adjustment system has recorded a cardiac function metric value for each of the incrementally adjusted pacing parameters ($AV_R$, $AV_L$, VV) within the predetermined adjustment range. Depending upon the implementation, the adjustment system preferably keeps all but one of the pacing parameters fixed while it incrementally adjusts the remaining free parameter. For example, the adjustment-system may hold $AV_R$ and $AV_L$ constant while adjusting the VV interval through the VV adjustment range and so on. In any case, once all adjustment ranges are complete, the adjustment system examines the recorded cardiac function metric, at step 512, to identify the optimal set of pacing parameters. Alternatively, the adjustment system may be preprogrammed to pick one particular cardiac function parameter, such a stroke volume, and then select the set of pacing parameters that achieves the maximum of that particular parameter.

At step 514, the adjustment system then paces the heart using the newly adjusted parameters for some fixed interval of time while continuing to monitor cardiac function to ensure that cardiac function is improved. In the unlikely event that no improvement has been gained as compared with the pre-adjusted parameters, then the pacing parameters are reset to their previous values and diagnostic signals are recorded indicating possible problems with the optimization procedure. In either case, processing then returns to FIG. 5.

Thus, an exemplary technique for optimizing biventricular pacing parameters has been described. In other examples, four chamber pacing parameters and multi-site pacing parameters are optimized (such as $A_R V_R$, $A_R V_L$, $A_L V_R$, and $A_L V_L$ parameters or $A_R V_{R1} V_{R2}$ and $A_R V_{L1} V_{L2}$ parameters. The specific manner by which the device automatically adjusts the pacing parameters and the specific indicators employed to trigger such adjustments are programmable by physician using the external programmer device shown FIG. 2. As can be appreciated, a wide range of techniques may be employed in accordance with the general invention for triggering the adjustment of pacing parameters and for making specific adjustments. No attempt made herein to set forth all possible techniques. Rather, only exemplary implementations are described.

In general, while the invention has been described with reference to particular embodiments, modifications can be made thereto without departing from the spirit and scope of the invention.

What is claimed is:

1. In an implantable cardiac stimulation device for implant within a patient, a method comprising:
    detecting heart sound signals;
    determining whether systolic regurgitant murmurs are occurring during an ejection period; and
    processing the heart sound signals to derive one or more parameters representative of cardiac function of the patient, wherein the one or more parameters comprise stroke volume, cardiac output, and maximum rate of change of aortic pressure over time.

2. The method of claim 1 wherein determining one or more parameters representative of cardiac function of the patient comprises:
    determining two or more parameters representative of cardiac function of the patient.

3. The method of claim 1 wherein detecting heart sound signals comprises:
    detecting acceleration signals representative of the acceleration of tissues within the patient; and
    converting the acceleration signals into heart sound signals.

4. The method of claim 3 wherein determining one or more parameters representative of cardiac function comprises:
    identifying S1 and S2 heart sounds within the heart sound signals.

5. The method of claim 3 further comprising detecting electrocardiographic signals representative of electrical characteristics of the heart.

6. The method of claim 5 wherein identifying S1 and S2 heart sounds comprises:
    detecting ventricular depolarization signals and ventricular repolarization signals within the electrocardiographic signals;
    defining S1 and S2 search windows within the heart sound signals subsequent to the ventricular depolarization and repolarization signals, respectively; and
    detecting the S1 and S2 heart sounds within, respectively, the S1 and S2 search windows.

7. The method of claim 6 wherein detecting the S1 and S2 heart sounds comprises rectifying the heart sound signals;

determining a maximum of the rectified heart sound signal within each of the S1 and S2 windows;

setting S1 and S2 detection thresholds based on the maximum of the rectified heart sound signals; and identifying the S1 and S2 heart sounds based on a comparison of the rectified heart sound signal within the detection thresholds within the respective S1 and S2 search windows.

8. The method of claim 6 further comprising detecting the duration of an ejection period based on the S1 and S2 heart sounds.

9. The method of claim 8 wherein detecting the duration of the ejection period is performed to determine the time interval from the end of the S1 sound to the beginning of the S2 sound.

10. The method claim 9 further comprising detecting heart rate based on the electrocardiographic signals.

11. The method of claim 10 further comprising detecting a maximum of the S1 heart sound (max_S1).

12. The method of claim 11 wherein determining whether systolic regurgitant murmurs are occurring during the ejection period comprises determining a peak to peak maximum of the heart sound signal during a murmur detection interval and comparing the maximum heart sound in the murmur detection interval to a pre-determined murmur detection threshold.

13. The method of claim 11 wherein determining one or more parameters representative of cardiac function comprises:

determining, if there are no systolic regurgitant murmurs during the ejection period, an isovolumic interval (ISOV) from the S1 heart sound.

14. The method of claim 13 wherein determining one or more parameters representative of cardiac function comprises:

estimating, if there are no systolic regurgitant murmurs during the ejection period, max dP/dt based on:

$$P\_max\_dP/dt = max\_S1/ISOV$$

wherein P_max_dP/dt is a predictor for max_dP/dt.

15. The method of claim 13 wherein determining one or more parameters representative of cardiac function comprises:

estimating, if there are no systolic regurgitant murmurs during the ejection period, max dP/dt based on:

$$P\_max\_dP/dt = 80 \text{ mm Hg}/ISOV$$

wherein P_max_dP/dt is a predictor for max dP/dt.

16. The method of claim 13 wherein determining one or more parameters representative of cardiac function comprises:

estimating, if there are no systolic regurgitant murmurs during the ejection period, stroke volume based on:

$$P\_SV = 11/18 * EJT\_prd * S1\_max/ISOV$$

wherein P_SV is a predictor for stroke volume.

17. The method of claim 16 wherein determining one or more parameters representative of cardiac function comprises:

estimating cardiac output based on:

$$P\_CO = P\_SV * \text{heart rate}.$$

18. The method of claim 13 wherein determining one or more parameters representative of cardiac function comprises:

estimating, if there are systolic regurgitant murmurs during the ejection period, max dP/dt based on:

$$P\_max\_dP/dt = max\_S1$$

wherein P_max_dP/dt is a predictor for max_dP/dt.

19. The method of claim 13 wherein determining one or more parameters representative of cardiac function comprises:

estimating, if there are systolic regurgitant murmurs during the ejection period, stroke volume based on:

$$P\_SV = 11/18 * EJT\_prd * S1\_max$$

wherein P_SV is a predictor for stroke volume.

20. The method of claim 19 wherein determining one or more parameters representative of cardiac function comprises:

estimating cardiac output based on:

$$P\_CO = P\_SV * \text{heart rate}.$$

21. The method of claim 3 wherein detecting signals representative of the acceleration of tissue within the patient comprises detecting internal acceleration signals.

22. The method of claim 21 wherein detecting acceleration signals comprises:

substantially filtering out all signals not representative of movement of the heart.

23. The method of claim 1 further comprising monitoring progression of heart failure in the patient by monitoring changes in parameters representative of cardiac function.

24. The method of claim 1 wherein the operation of the implantable stimulation device is controlled by control parameters and further comprising adjusting the control parameters based the parameters representative of cardiac function.

25. The method of claim 24 wherein adjusting the control parameters comprises:

adjusting the control parameters so as to resynchronize the ventricles.

26. The method of claim 24 wherein adjusting the control parameters is performed to adjust one or more of monoventricular pacing control parameters, biventricular pacing control parameters, four-chamber pacing control parameters or individual chamber multi-site pacing control parameters.

27. In an implantable cardiac stimulation device for implant within a patient, a system comprising:

means for detecting acceleration signals representative of the acceleration of tissues within the patient; and means for converting the acceleration signals into heart sound signals means for detecting systolic regurgitant murmurs during an ejection period; and means for processing the heart sound signals to derive one or more parameters representative of cardiac function of the patient, wherein the one or more parameters comprise stroke volume, cardiac output, and maximum rate of change of aortic pressure over time.

28. The system of claim 27, and further comprising means for adjusting operation based on the one or more parameters.

* * * * *